United States Patent
Kitamura et al.

(10) Patent No.: US 6,194,380 B1
(45) Date of Patent: Feb. 27, 2001

(54) AGENTS FOR PROMOTING BONE FORMATION

(75) Inventors: Kazuyuki Kitamura, Saitama; Osamu Komiyama, Tokyo; Mizuho Inazu, Saitama, all of (JP); Roland Baron, Paris (FR); Thomas R. Gadek, Oakland, CA (US); Hans-Ulrich Stilz, Frankfurt Am Main (DE); Volkmar Wehner, Sandberg (DE); Jochen Knolle, Kriftel (DE); Robert S. McDowell, San Francisco, CA (US)

(73) Assignee: Hoechst Marion Roussel (FR)

( * ) Notice: Subject to any disclaimer, the term of this patent is extended or adjusted under 35 U.S.C. 154(b) by 0 days.

(21) Appl. No.: 09/077,714

(22) PCT Filed: Dec. 6, 1996

(86) PCT No.: PCT/EP96/05380

§ 371 Date: Apr. 20, 1999

§ 102(e) Date: Apr. 20, 1999

(87) PCT Pub. No.: WO97/21726

PCT Pub. Date: Jun. 19, 1997

(30) Foreign Application Priority Data

Dec. 8, 1995 (JP) .................................................. 7-345057

(51) Int. Cl.$^7$ ............................ A01N 37/18; A61K 38/00
(52) U.S. Cl. ................................... 514/2; 514/9; 514/11; 514/12; 514/13; 514/14; 514/15; 514/16; 514/17; 514/18
(58) Field of Search ................................ 514/12, 9, 2, 11, 514/13, 14, 15, 16, 17, 18; 530/317, 300, 324, 325, 326, 327, 328, 329, 330, 331

(56) References Cited

U.S. PATENT DOCUMENTS

| | | | |
|---|---|---|---|
| 5,384,309 | 1/1995 | Barker et al. ......................... | 514/11 |
| 5,384,309 * | 1/1995 | Barker et al. ......................... | 514/11 |

FOREIGN PATENT DOCUMENTS

| | | |
|---|---|---|
| 0528586 | 2/1993 | (EP) . |
| 0530505 | 3/1993 | (EP) . |
| 9514008 | 5/1995 | (WO) . |
| 9600240 | 1/1996 | (WO) . |

OTHER PUBLICATIONS

Barker et al, "Cyclic . . . Antithrombotics", J. Med. Chem., vol. 35, 1992, pp. 2040–2048, XP002029505.

Horton, et al "Arg–Gly–Asp (RGD) . . . Osteoclasts" Experimental Cell Research, vol. 195, 1991, pp. 368–375, XP000651755.

King et al, "Effects . . . In Vivo", J. Bone and Mineral Res., vol. 9, No. 3, 1994, pp. 381–387, XP000652637.

Oursler M.J. and Th.C. Spelsberg, "Editorial: Echistatin . . . Osteoporosis", Endocrinology, vol. 132, No. 3, 1993, Baltimore, pp. 939–940, XP000652637.

Fisher et al, "Inhibition . . . (RGD)_Containing Protein", vol. 132, No. 3, 1993, Baltimore, pp. 1411–1413, XP000652599.

Van Der Pluijm et al, "Integrins . . . Osteoclast Formation", J. Bone and Mineral Res., vol. 9, No. 7, 1994, pp. 1021–1028, XP000651794.

Dresner–Pollak et al, "Blockade . . . of Osteoporosis", J. Cellular Biochem., vol. 56, 1994, pp. 323–330, XP000652575.

Fisher et al, *Endocrinology*, vol. 132, No. 3, 1993, pp. 1411–1413.*

* cited by examiner

*Primary Examiner*—Avis M. Davenport
(74) *Attorney, Agent, or Firm*—Bierman, Muserlian and Lucas

(57) ABSTRACT

The object is to provide a promoting agent for bone formation, a therapeutic method for bone formation and a process for preparing a promoting agent for bone formation.

A promoting agent for bone formation which comprises at least one of kistrin, echstatin, a peptide or polypeptide containing the amino acid sequence ArgGlyAsp in the molecule such as a peptide represented by Gly-Arg-Gly-Asp-Ser or a compound represented by the following general formula (IX) and so on, as well as a biologically acceptable salt thereof (IX)

$$R_{16}-(CH_2)_a-\underset{\underset{R_{17}}{|}}{N}\underset{O}{\overset{O}{\|}}N-(CH_2)_b-\underset{\underset{O}{\|}}{C}-NH-\underset{\underset{(CH_2)_c}{|}}{CH}-\underset{\underset{(NH)_e}{|}}{C}-Y-\underset{\underset{R_{19}}{|}}{CH}-R_{18}$$

(with COOH on $(CH_2)_d$ branch)

wherein $R_{16}$ represents —N$(R_{20})_2$ ($R_{20}$ represents a hydrogen atom or a $C_1$–$C_4$ alkyl group), $R_{17}$ represents a hydrogen atom or a $C_1$–$C_4$ alkyl group, $R_{18}$ represents a hydrogen atom, a $C_1$–$C_4$ alkyl group and so on, $R_{19}$ represents OH, NH$_2$ and so on, Y represents —NH—, —O— or a direct bond, a represents 1–3, b represents 1 or 2, c represents 0 or 1 and d represents 0 or 1.

13 Claims, No Drawings

AGENTS FOR PROMOTING BONE FORMATION

This application is a 371 of PCT/EP96/05380 field Dec. 6, 1996.

This invention relates to a promoting agent for bone formation which comprises a peptide or polypeptide containing the amino acid sequence consisting of ArgGlyAsp (hereinafter referred to as RGD sequence) in the molecule. Further, the invention relates to a prophylactic and therapeutic method for bone fracture utilizing a promoting agent for bone formation comprising the peptide or polypeptide containing the said RGD sequence. Also, the invention relates to a novel cyclic peptide containing the said RGD sequence. And further, it relates to a promoting agent for bone formation which comprises a compound represented by the general formulae (IX), (X), (XI) and (XII).

Bone is composed of outer cortical bone and inner trabecular bone. The function of bone in living body is to maintain a given shape as a skeleton and to store various inorganic substances such as calcium, phosphoric acid and the like. Bone may apparently appear to be a tissue with less variability, but actually old bone is adsorbed and instead new bone is formed. This is usually referred to as bone reformation. The bone reformation can be accomplished by coupling of osteoclasts controlling bone adsorption with osteoblasts controlling bone formation as both can primarily participate in therein. It has been recently elucidated that the function of osteoblasts is not limited to bone formation solely, but it is related to differentiation and activation of osteoclasts and osteoblasts may play a role as a control center in cellular bone reconstruction.

Those diseases generally referred to as bone metabolism diseases may include osteoporosis, Behget disease, osteomalacia, hyperostosis and osteopetrosis. Among them, osteoporosis is the most frequently developed disease and frequency of its occurrence appears to increase with senescence so that the diagnosis and effective therapy thereof have been earnestly desired.

The bone metabolism diseases mean those diseases wherein bone cells have specific metabolic abnormalities in any bone tissues. The present inventors have made earnest studies to find out a promoting factor for bone formation using a cultural assay and finally completed this invention.

Integrin may participate in the interaction between cells and cells or between cells and extracellular matrices and play an important role in wound healing, development, immunization, hemostasis or metastasis. Integrin superfamily is an α,β-heterodimer group found on the cell surface and may combine extracellular ligands and cytoskeleton. All integrins are heterodimers and each sub-unit is extracellular by 90% and may have a long membrane permeable domain and a short intracellular domain. The extracellular domain is bound with the extracellular matrices or ligands of the cell surface, while the intracellular domain is bound with cytoskeleton proteins. Bone matrices such as osteopontin, bone sialoglycoproteins, thrombospondin, fibronectin and vitronectin are found in bone and all proteins have been found to have the RGD sequence. Recently, osteoclasts have been found to have integrin αVβ3 and α2β1 in the cell membrane surface (Davies J. et al., J. Cell Biol., Vol.1, 109, p.1817, 1989 and Zambonin Z. A. et al., Connect. Tissue Res., Vol.20, p.143, 1989). From the facts that bone absorption by osteoclasts can be inhibited by the action of an antibody to integrin (Davies J. et al., J. Cell Biol., Vol.109, p.1817, 1989), that bone absorption by rat osteoclasts can be inhibited by synthetic GRGDSP peptide (GlyArgGlyAspSerPro) (Horton M. A. et al., Exp. Cell Res., Vol.195, p.368, 1991), and further that echstatin, a protein derived from snake venom and having the RGD sequence and a platelet aggregation inhibiting activity, a synthetic GdRGDSP peptide and a cyclic synthetic GPenGRGDSPCA peptide can inhibit bone absorption by mouse osteoclasts and GdRGDSP peptide can inhibit the formation of tartaric acid-resistant and phosphatase-positive multinuclear osteoclasts (Gabri V. D. P. et al., J. Bone Miner. Res., Vol.9, p.1021, 1994), it is suggested that recognition and adhesion of bone matrices by integrin and related cytoskeleton does deeply participate in the development of bone absorption function of osteoclasts.

It may be then considered that the adhesion of cell matrices between osteoblasts and bone matrices would be caused by the adhesion mechanism via collagen and fibronectin in the bone matrices and β1 integrin of osteoblasts. Also, it would be possible in the adhesion mechanism between heterocytes that the cell adhesion of osteoblasts with osteoclasts can be performed via fibronectin as both β3 integrin of osteoclasts and β1 integrin in osteoblasts may be a receptor for fibronectin. However, it has not yet been suggested that the disintegrin family including echstatin or kistrin (William R. G. et al., Protein Science, Vol.2, p.1749, 1993) and the RGD peptide show a promoting action for bone formation.

It is the object of this invention to provide a promoting agent for bone formation, a therapeutic method for bone formation and a process for preparing a promoting agent for bone formation.

Bone formation can be promoted by administering a peptide or polypeptide containing the RGD sequence in the molecule or a biologically acceptable salt thereof to patients. The peptides or polypeptide containing the RGD sequence in the molecule may illustratively include kistrin, echstatin, a peptide represented by Gly-Arg-Gly-Asp-Ser (hereinafter referred to as GRGDS (SEQ ID NO: 1)), a compound represented by the general formula (I)

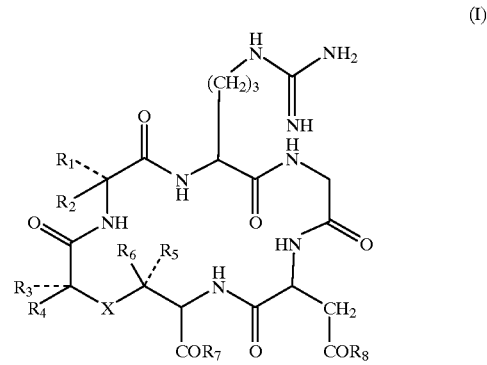

wherein $R_1$, $R_2$, $R_3$, $R_4$, $R_5$ and $R_6$ may be the same or different and each represents one selected from the group consisting of a hydrogen atom; an alkyl group of 1–8 carbon atoms optionally substituted with one selected from the group consisting of a hydroxy group, a carboxy group, a cycloalkyl group of 3–10 carbon atoms optionally substituted with a hydroxy group, and an aryl group of 6–12 carbon atoms optionally substituted with a hydroxy group ; a cycloalkyl group of 3–10 carbon atoms optionally substituted with hydroxy group and an aryl group of 6–12 carbon atoms optionally substituted with a hydroxy group, $R_7$ and $R_8$ may be the same of different and each represents a group selected from the group consisting of a hydroxy group, an alkoxy group of 1–8 carbon atoms, an alkenyloxy group of 2–12 carbon atoms, a cycloalkyloxy group of 3–10 carbon atoms and an aryloxy group of 6–12 carbon atoms, and X represents S or $SO_2$ and a compound represented by the general formula (II)

(II)

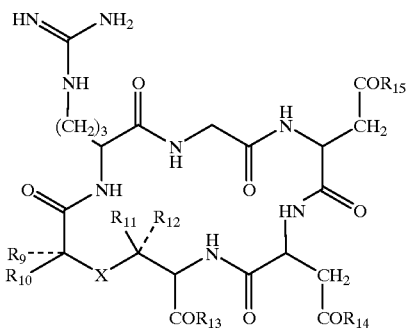

wherein $R_9$, $R_{10}$, $R_{11}$ and $R_{12}$ may be the same or different and each represents one selected from the group consisting of a hydrogen atom, an alkyl group of 1–8 carbon atoms, a cycloalkyl group of 3–10 carbon atoms and an aryl group of 6–12 carbon atoms optionally substituted with a hydroxy group, $R_{13}$, $R_{14}$ and $R_{15}$ may be the same or different and each represents a group selected from the group consisting of a hydroxy group, an alkoxy group of 1–8 carbon atoms, an alkenyloxy group of 2–12 carbon atoms, a cycloalkyloxy group of 3–10 carbon atoms and an aryloxy group of 6–12 carbon atoms, and X represents S or SO.

And, this invention provides a new compound represented by the formula (II).

Also, this invention is directed to a therapeutic method for promoting bone formation which comprises administering to patients a compound represented by the general formula (IX)

(IX)

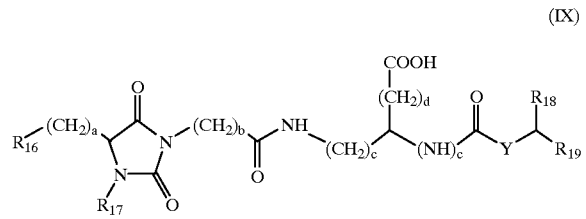

wherein $R_{16}$ represents $—N(R_{20})_2$, $—C(=NH)—NH_2$, $—NH—C(=NH)—NH_2$ or $—CO—NH—C(=NH)—NH_2$ (in which $R_{20}$ independently represents a hydrogen atom or an alkyl group of 1–4 carbon atoms optionally substituted with a phenyl group), $R_{17}$ represents a hydrogen atom or an alkyl group of 1–4 carbon atoms optionally substituted with a phenyl group, $R_{18}$ represents a hydrogen atom, an alkyl group of 1–4 carbon atoms, a phenyl group optionally substituted with a methoxy group or $—COR_{21}$ (in which $R_{21}$ represents $—OH$, $—NH_2$, $—NH—(CH_2)_2$-phenyl, an alkoxy group of 1–3 carbon atoms, a benzyloxy group, Pro or Aoc), $R_{19}$ represents an alkyl group of 1–5 carbon atoms optionally substituted with a substituent selected from the group consisting of OH, $—NH_2$, $—CONH_2$, cyclohexyl, phenyl, naphthyl, indolyl or adamantyl, a methyl group substituted with $—COOH$ and $—NHCOOCH_2$-phenyl group, a cyclohexyl group optionally substituted with a methoxy group or an aryl group of 6–10 carbon atoms optionally substituted with a methoxy group, provided that $R_{18}$ and $R_{19}$ together with the carbon atoms to which they are attached may form adamantyl, naphthyl or fluorenyl, Y represents $—NH—$, $—O—$ or a direct bond, a represents 1, 2 or 3, b represents 1 or 2, c represents 0 or 1 and d represents 0 or 1, a compound represented by the general formula(X)

(X)

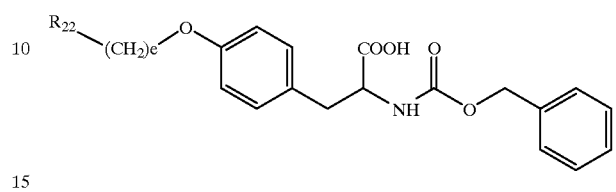

wherein $R_{22}$ represents $—N(R_{23})_2$, $—C(=NH)NH_2$, $—NH—C(=NH)—NH_2$ or $—CO—NH—C(=NH)—NH_2$ (in which $R_{23}$ independently represents a hydrogen atom or an alkyl group of 1–4 carbon atoms optionally substituted with a phenyl group) and e represents 2–6, a compound of the formula (XI)

(XI)

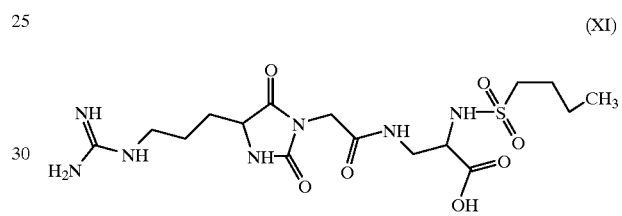

or a compound of the formula (XII)

(XII)

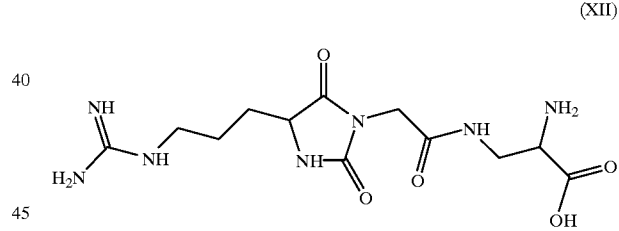

or a biologically acceptable salt thereof.

In the above formulae, Pro and Aoc represent respectively

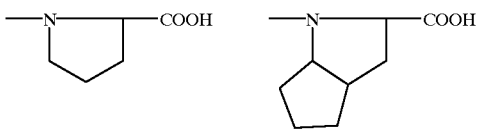

Kistrin and echstatin are proteins having molecular weights of about 7,300 and about 5,400, respectively, and they are disclosed, for instance, Protein Science (1993), 2, 1749–1755. The GRGDS (SEQ ID NO: 1) may be easily synthesized according to a conventional peptide synthesis. The compounds of the general formula (I) are disclosed in U.S. Pat. No. 5,384,309 and their representative compounds may be illustrated by the formulae (III)–(VI).

(III) 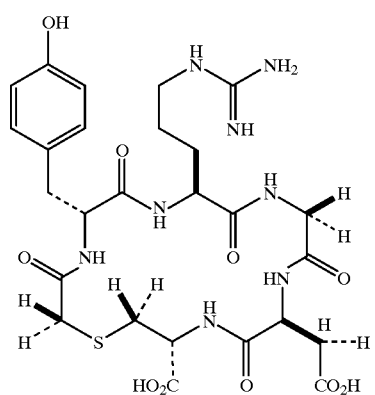
(IV) 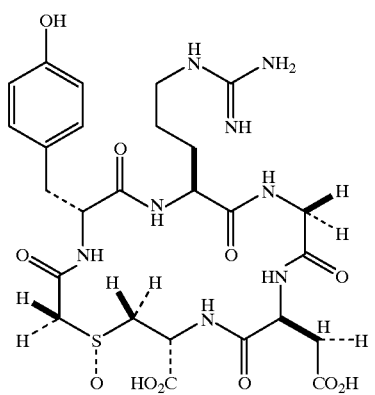
(V) 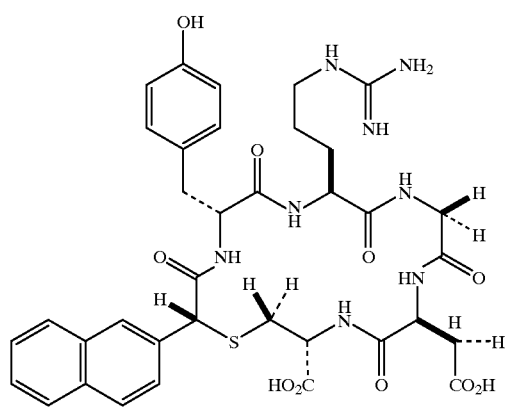
(VI) 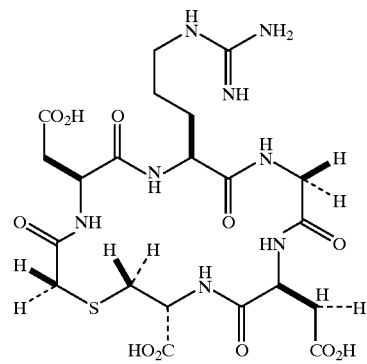
The compounds of the general formula (II) are novel and may be prepared according to the method as described in Barker et al., J.Med.Chem., 1992, 35,2040. Their representative compounds may be illustrated by the formulae (VII) and (VIII).
(VII) 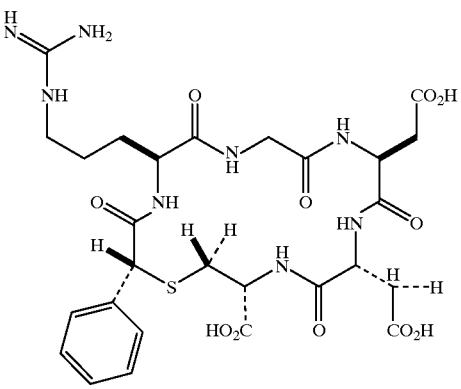
(VIII) 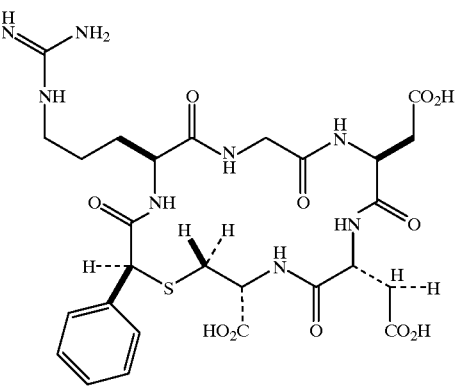

Illustrative compounds of the general formula (IX) are as recited below.
Compound n°1
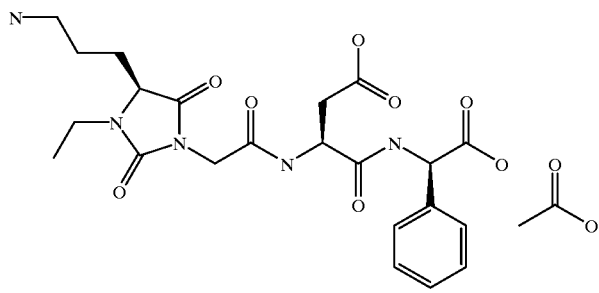
Compound n°2
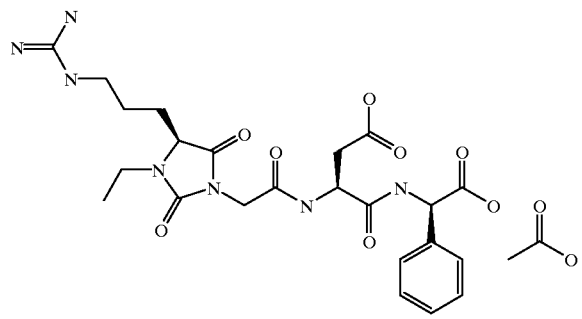
Compound n°3
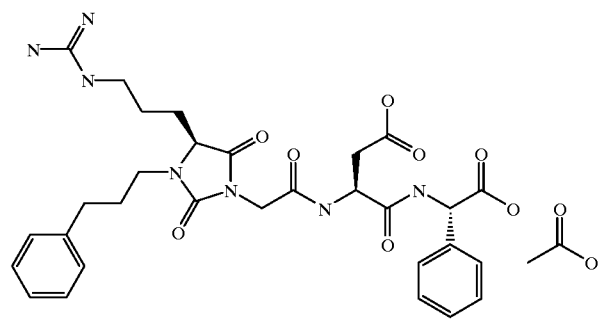
Compound n°4
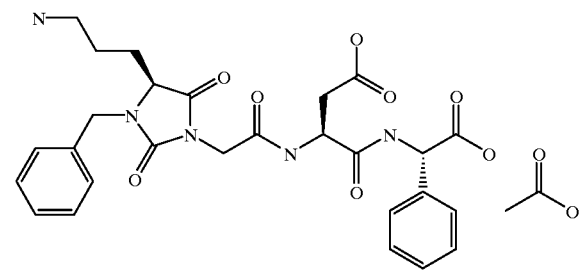
Compound n°5
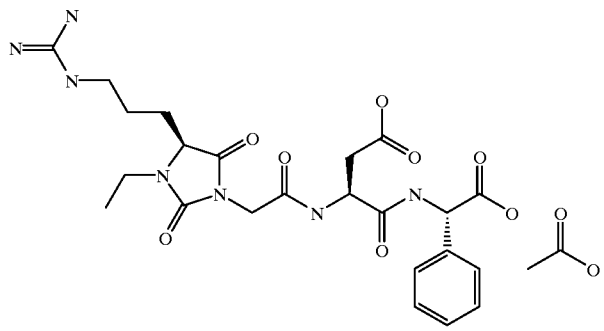
Compound n°6
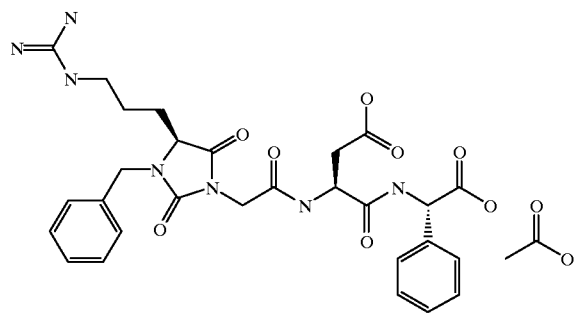
Compound n°7
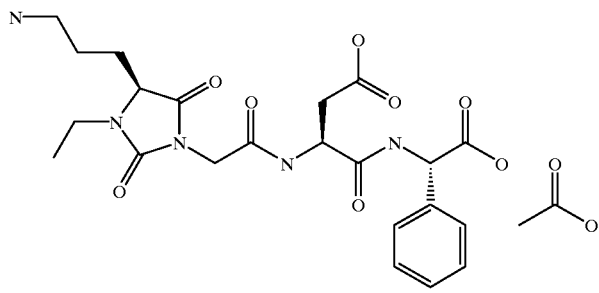
Compound N°8
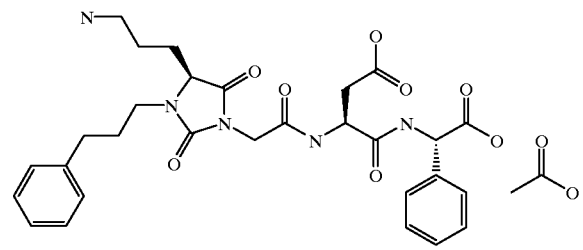

-continued
Compound n°9
Compound n°10
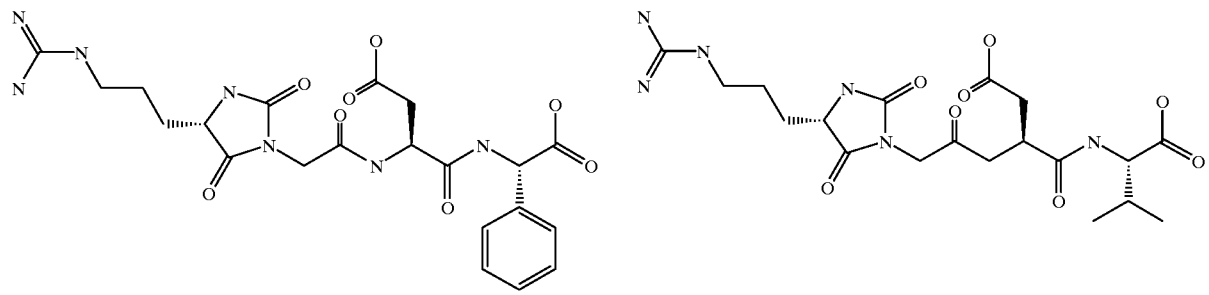
Compound n°11
Compound n°12
Compound n°13
Compound n°14
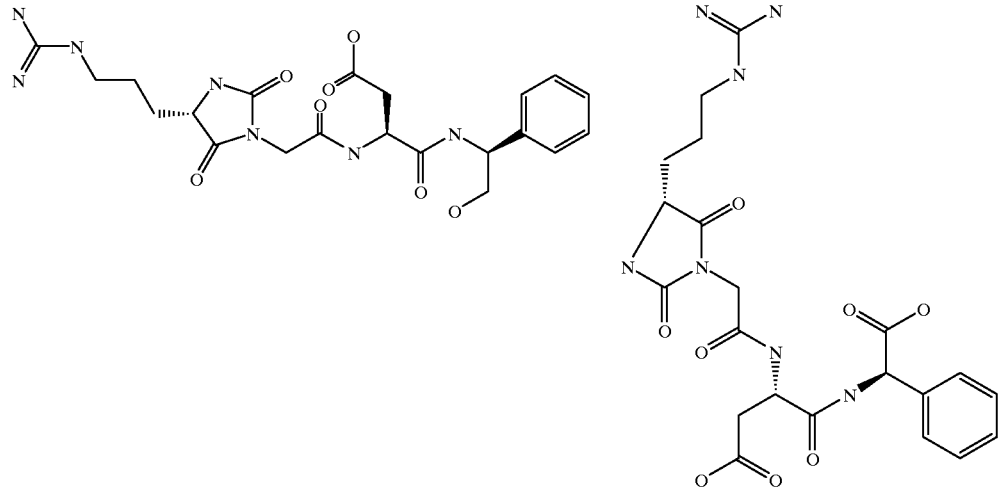
Compound n°15
Compound n°16
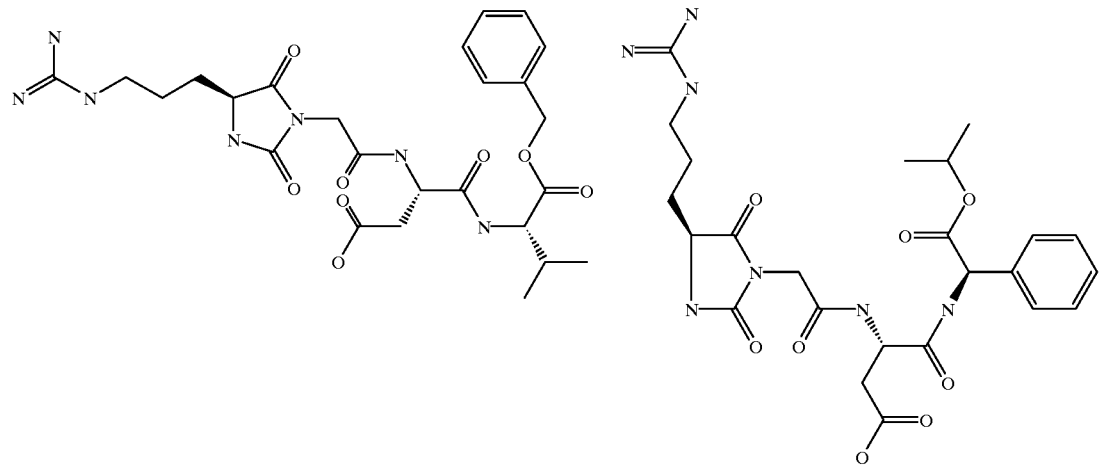

-continued
Compound n°17
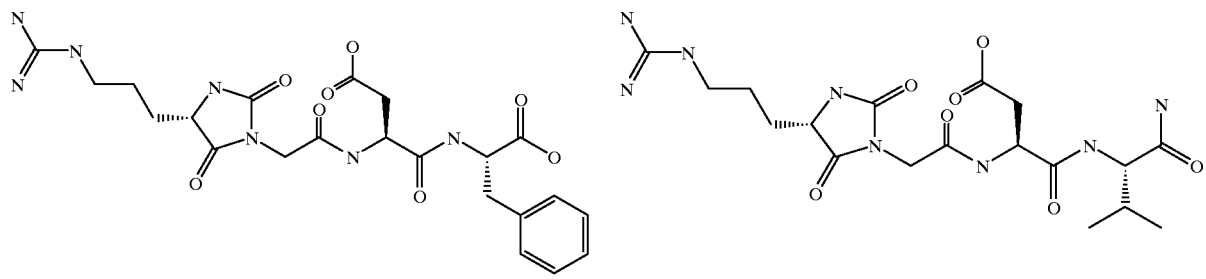
Compound n°18
Compound n°19
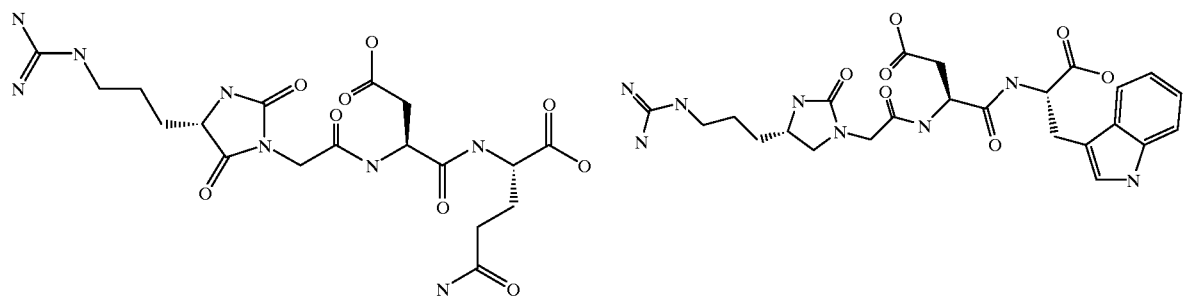
Compound n°20
Compound n°21
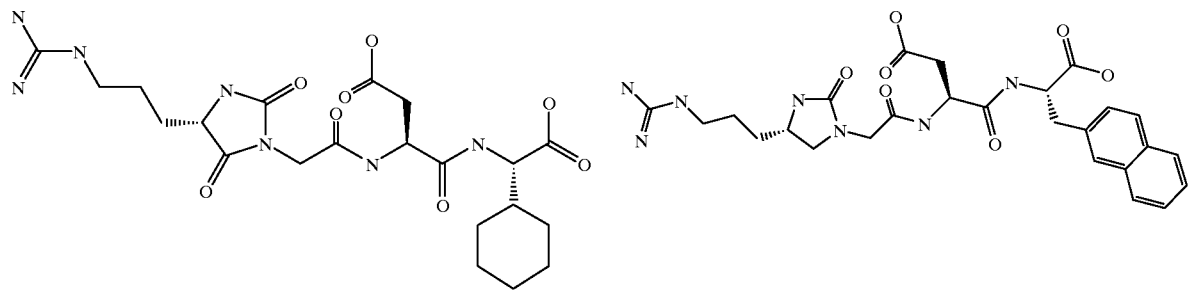
Compound n°22
Compound n°23
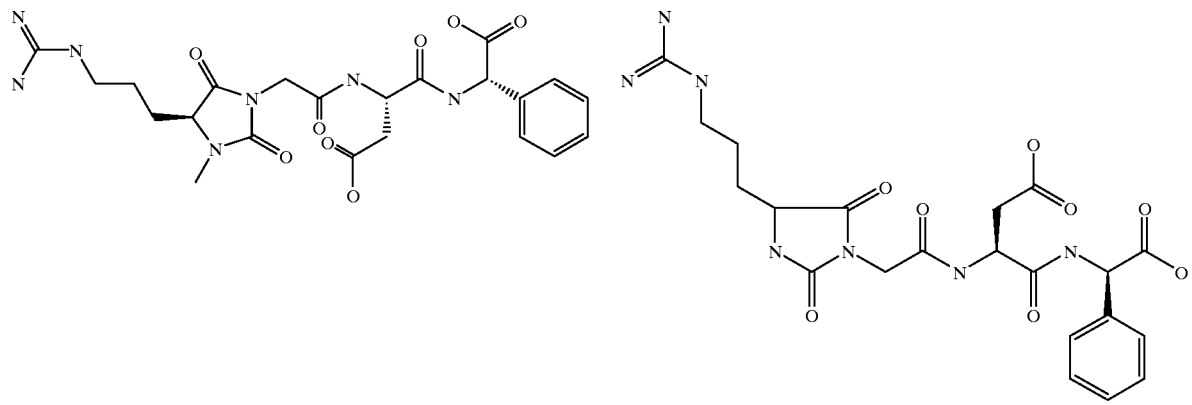
Compound n°24

-continued
Compound n°25
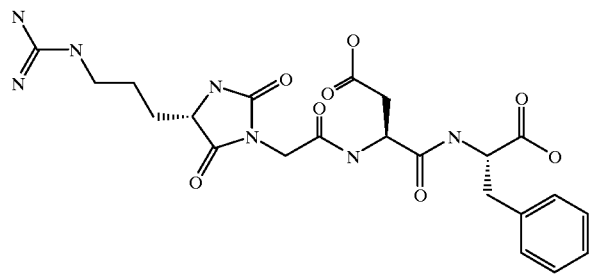
Compound n°26
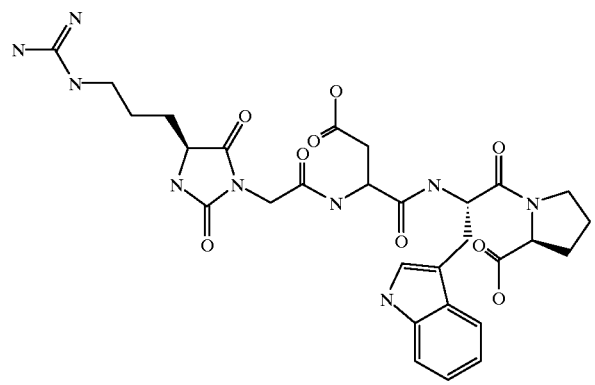
Compound n°27
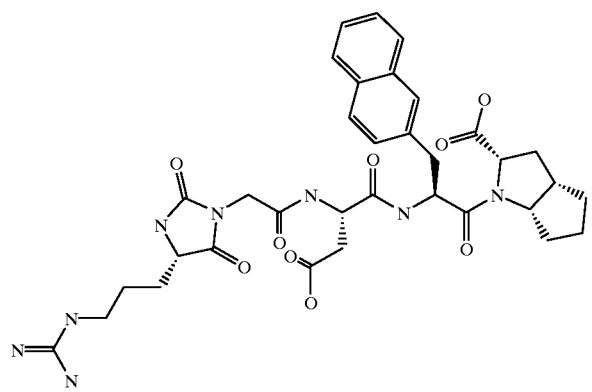
Compound n°28
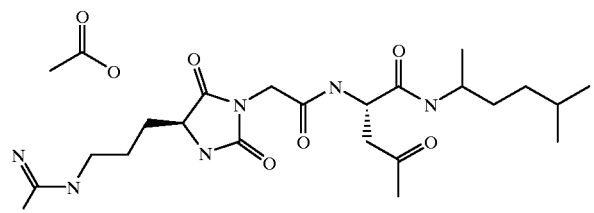
Compound n°29
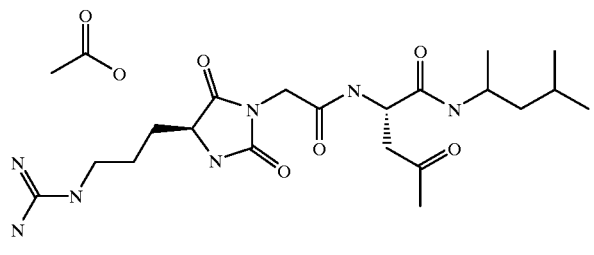
Compound n°30
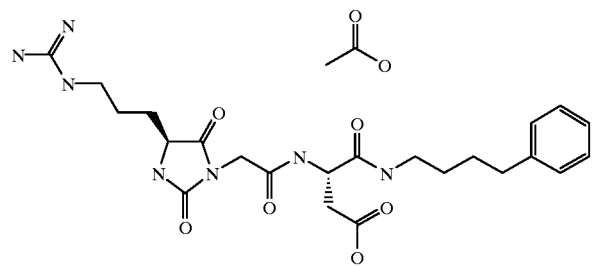
Compound n°31
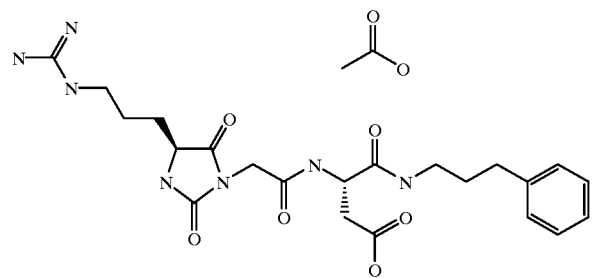
Compound n°32
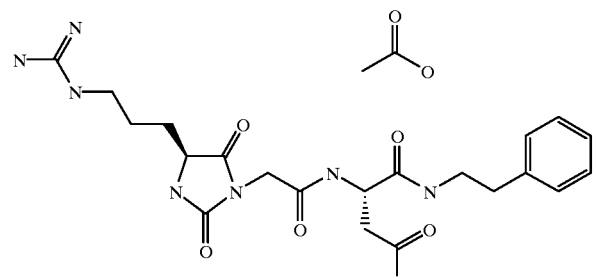

-continued
Compound n°33
Compound n°34
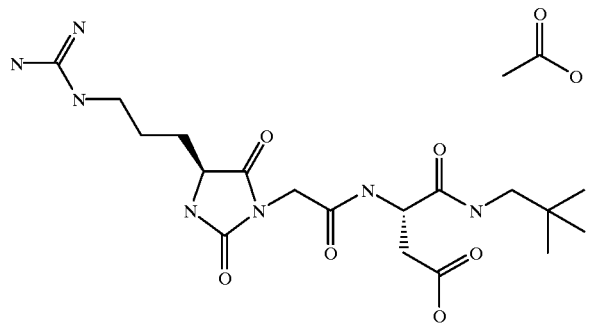
Compound n°35
Compound n°36
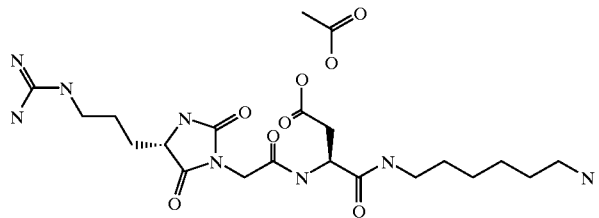
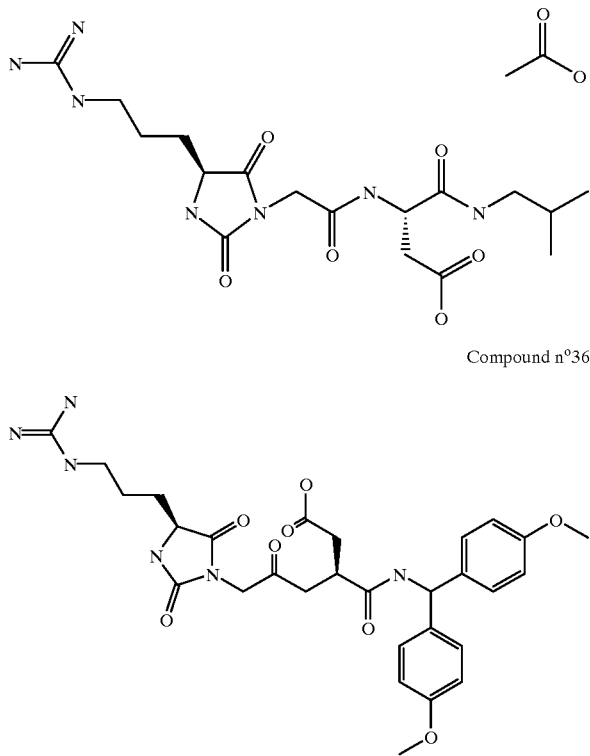
Compound n°37
Compound n°38
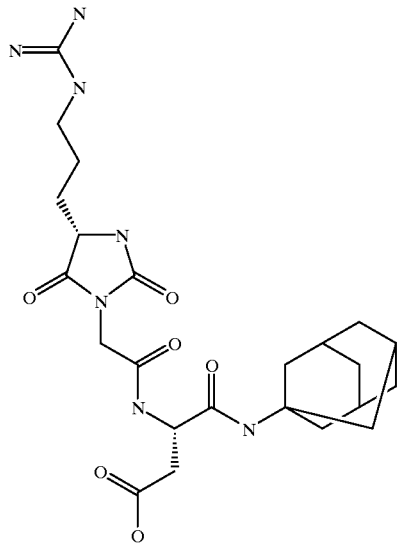
Compound n°39
Compound n°40
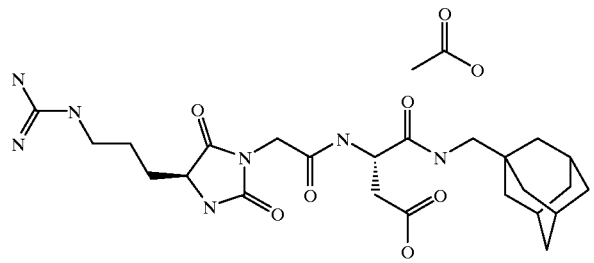
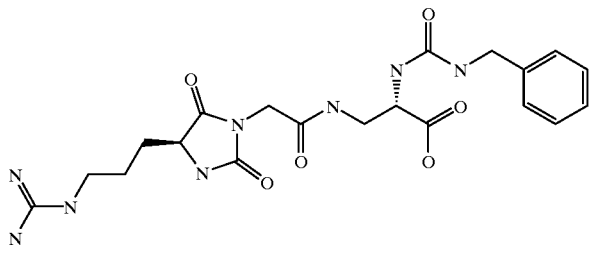

-continued
Compound n°41
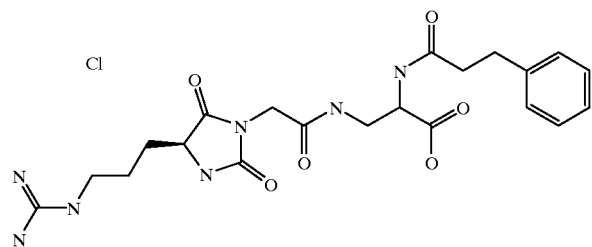
Compound n°42
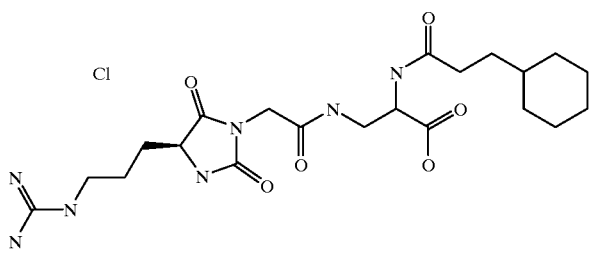
Compound n°43
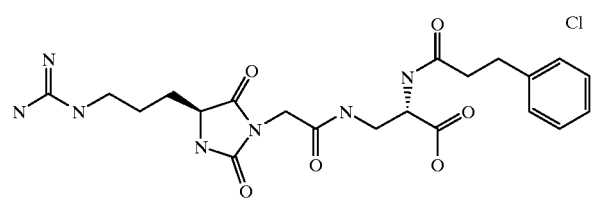
Compound n°44
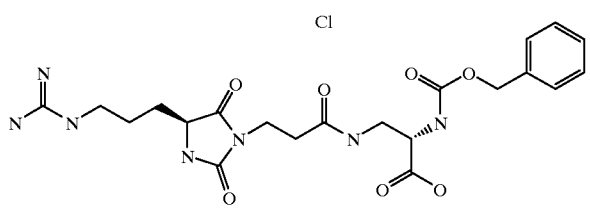
Compound n°45
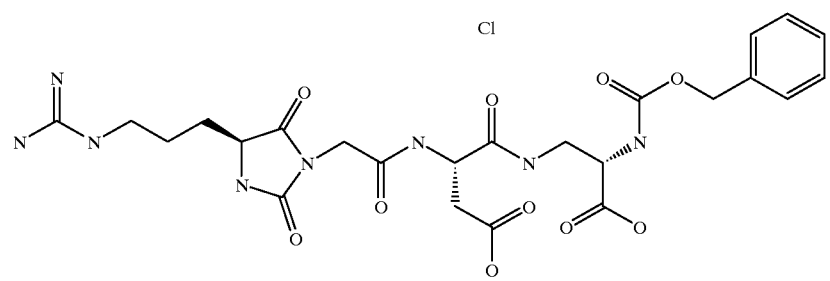
Compound n°46
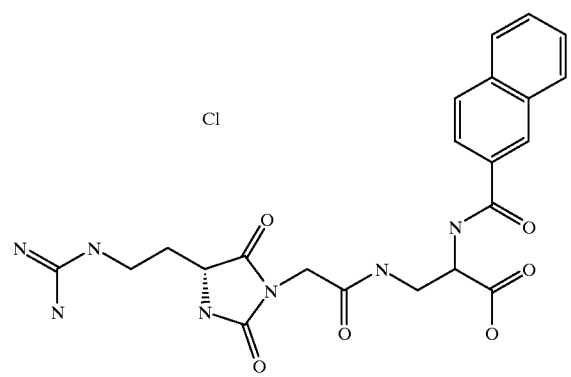
Compound n°47
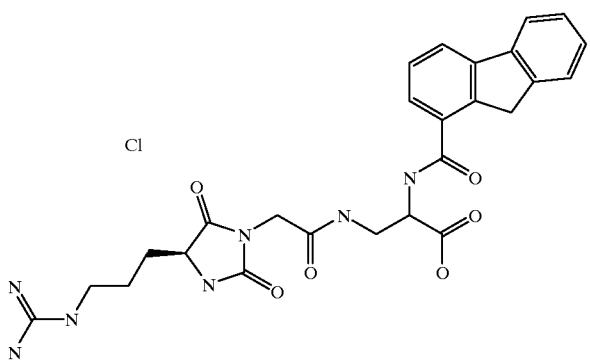

Compound n°48
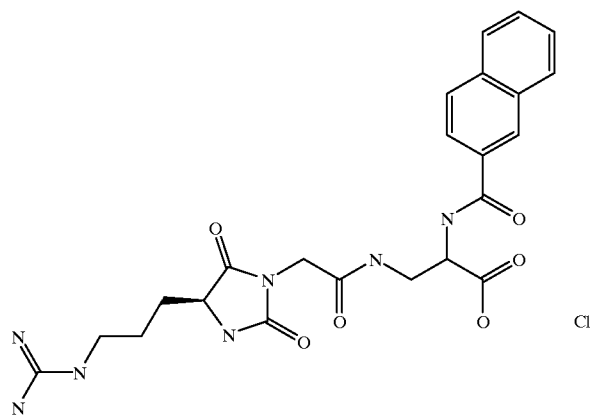
Compound n°49
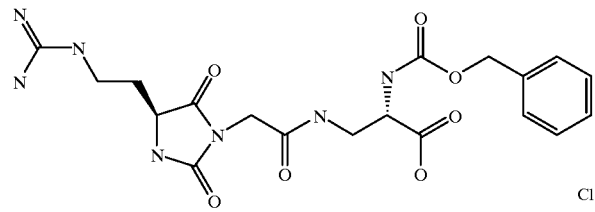
Compound n°50
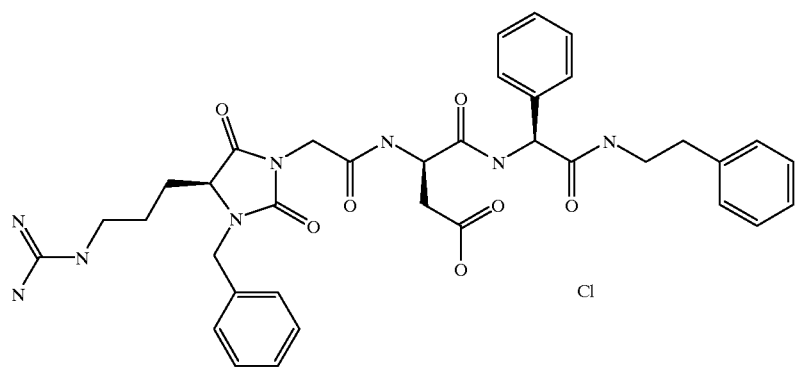
Compound n°51
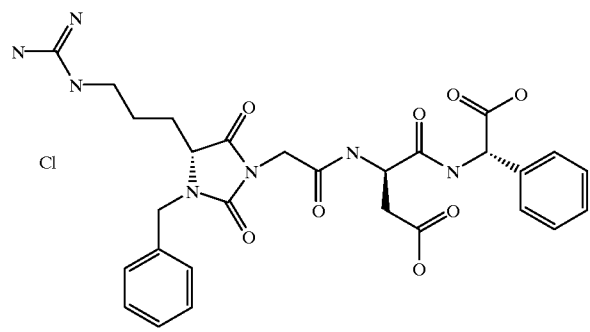
Compound n°52
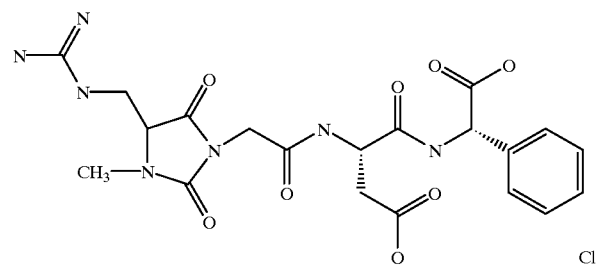

Illustrative compounds of the general formula (X) are as recited below.
Compound n°53
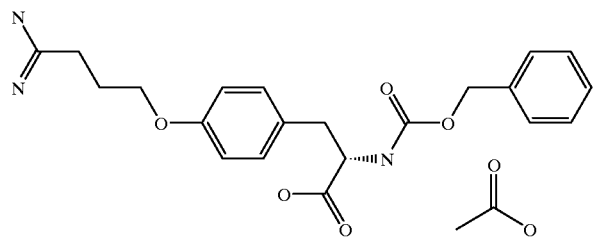
Compound n°54
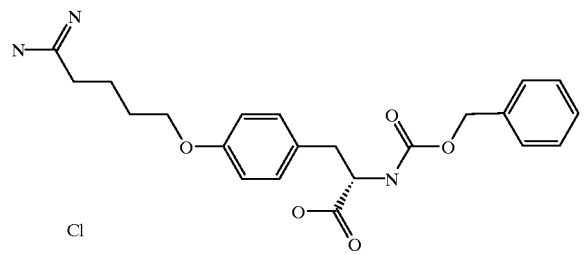
Compound n°55
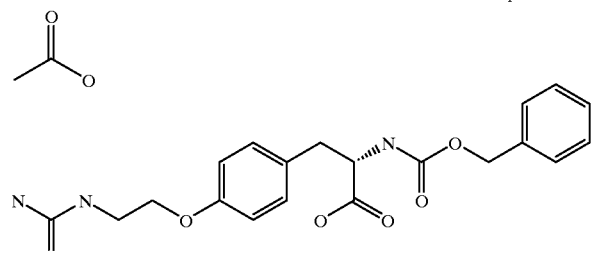
Compound n°56
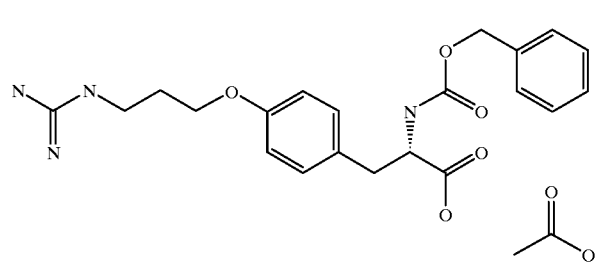
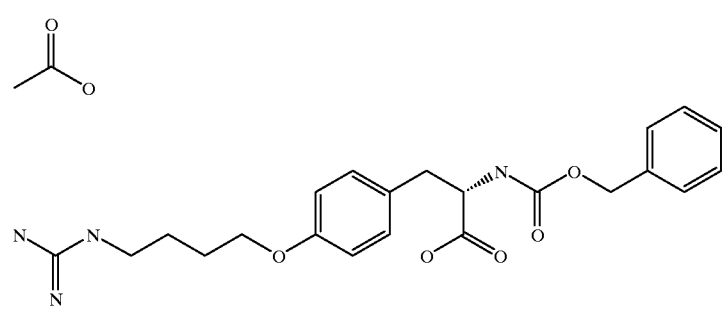
Compound n°57
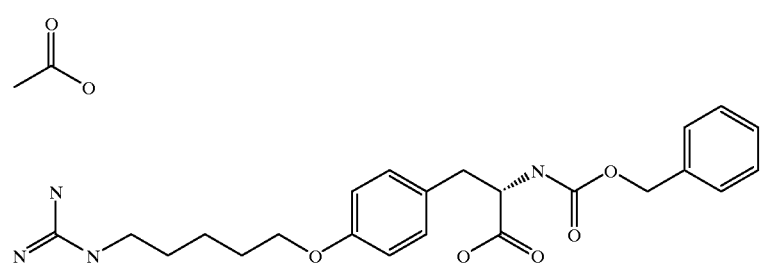
Compound n°58
Compound n°59
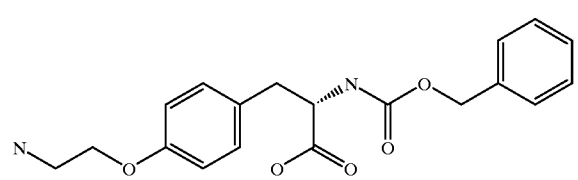
Compound n°60
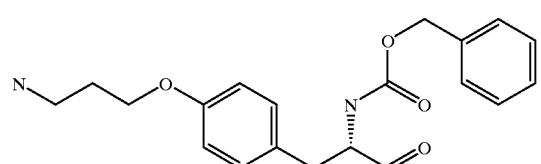
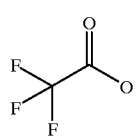

Compound n°61

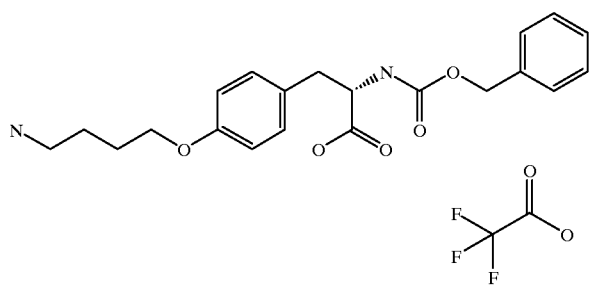

Compound n°62

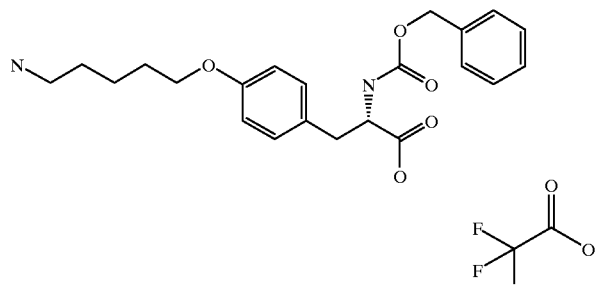

Compound n°63

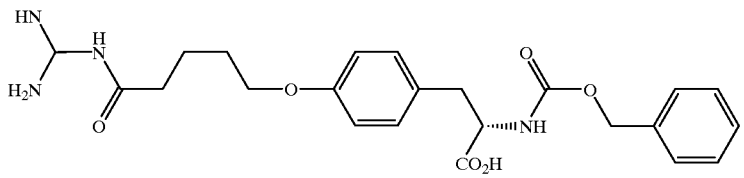

Illustrative compound of the general formula (XI) is as recited below.
Compound n°64

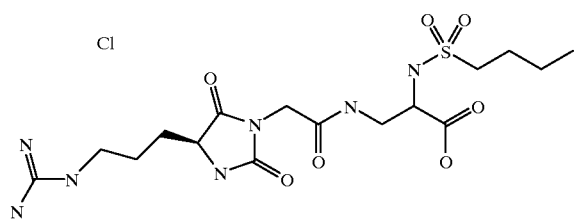

Illustrative compound of the general formula (XII) is as recited below.
Compound n°65

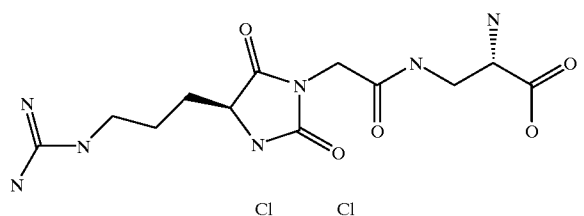

The compounds of the general formulae (IX), (X), (XI) and (XII) are known and may be synthesized according to the methods disclosed in EP-A0499079, EP-A0530505, EP-A0566919, WO 95/14008, EP-A0528586 and WO 93/19046. When kistrin or echstatin is to be administered to human as a promoting agent for bone formation, a daily dose of 0.001–100 μg/kg body weight, preferably 0.01–10 μg/kg body weight, is used. In the case of the GRGDS (SEQ ID NO: 1), a daily dose of 0.001–10 mg/kg body weight, preferably 0.01–1 mg/kg body weight, is used. In the case of the compound represented by the general formula (I), (II), (IX), (X), (XI) or (XII), a daily dose of 0.001–10 mg/kg body weight, preferably 0.01–1 mg/kg body weight, is used.

The present drug may be systemically administered by intravenous injection, intramuscular injection, intraperitoneal injection, oral administration, parenteral administration such as suppository or any other prior art means. As pharmaceutical preparations, there may be intended injectable or oral pharmaceutical preparations. Injectable pharmaceutical preparations may include, for example, injectable powders. In this instance, one or more of suitable water-soluble excipients such as mannitol, sucrose, maltose, glucose and fructose may be added and dissolved in water and the solution is poured portionwise into ampoules and freeze-dried and sealed to form pharmaceutical preparations. Oral pharmaceutical preparations may include conventional tablets, capsules, granules, fine granules, powders as well as enteric coated preparations.

In the treatment of bone fracture, it may be systemically administered or locally given by injection and others. For local administration, a carrier containing the present drug may be more preferably implanted in the area close to the fractured portion. In this case, natural polymeric substances such as collagen or fibrin glue, synthetic polymeric substances capable of being dispersed in living body such as poly lactated glycolic acid can be used for carriers. In plastic surgery, cosmetic surgery, bone transplantation or dental transplantation, the present agent may be applied by coating on the surface of the bone or tooth to be transplanted with an adhesive substance such as collagen paste or fibrin glue. And, it may be applied to the tissue, the bone or alveolar bone in the portion to which bone or tooth is to be transplanted. In transplantation of bone or tooth, artificial bone or artificial fang may be used which is composed of, for example, metals, ceramics, glass and other natural or artificial inorganic substances such as hydroxyapatite. In this case, it may be also feasible to form a core portion with a dense material and form a surface portion with a porous material such as hydroxyapatite and to penetre the present agent into the porous portion. Also, it is possible that the surface of artificial bone composed of a denser materials is roughened to keep the present agent over the said surface.

EXAMPLE

Synthesis Example of the Compounds GH 4 and GH 5

The Compounds GH 4 and GH 5 were prepared according to the standard FMOC method as described in P. L. Barker et al., J.Med.Chem., 35, p. 2040–2048, 1992. FMOC-S-trityl-cysteine bound to Wang resin was used as a starting material and the FMOC amino acid having a suitable side chain protecting group, D-aspartic acid(O-t-butyl); L-aspartic acid(O-t-butyl); glycine; L-arginine(N-2,2,5,7,8-pentamethylchromane-6-sulfonyl) were in turn used in 3 moles portions. The FMOC at the N-terminal was removed with piperidine (in the form of a 20% solution in dimethylacetamide) and racemic 2-bromo-2-phenylacetic acid (4 equivalents) activated with diisopropylcarbodiimide (2 equivalents) was added to the free N-terminal. The S-trityl group at the cysteine side chain was removed with a chloromethane solution containing dilute trifluoroacetic acid (2%) and then the resulting peptide was cyclized by addition of a solution of diisopropylethylamine (2 equivalents) in dimethylacetamide. Deprotection and sectioning of the cyclized peptide were performed by treatment with trifluoroacetic acid containing triethylsilane (2%). Removal of triethylfluoroacetic acid afforded a crude peptide, which was then purified using reverse phase HPLC column [Vydac, C-18, a 0.1% aqueous solution of trifluoroacetic acid, acetonitrile] with linear gradient (acetonitrile: 0–40%, 80 min). The compounds involved in those fractions obtained after about 22 minutes and about 24 minutes, respectively, were named GH 4 and GH 5. The peptides were isolated as white powders by freeze-drying in water. Both compounds were detected for molecular ion peak $(M+H)^+=680.7$ in electrospray mass spectra. Both compounds showed apparently different NMR spectra at 0–10 ppm in water at pH 4–5.
Coupling Constant(NH—CH, Hz)

| Amino acid | GH 4 | GH 5 |
| --- | --- | --- |
| Arginine | 8.05 | 4.9 |
| D-Aspartic acid | 8.02 | 8.1 |
| L-Aspartic acid | 3.14 | 7.7 |
| Cysteine | 6.08 | 7.6 |

GH 4 and GH 5 were confirmed to have the formula (VII) or (VIII), but could not be identified whichever they correspond to.

Preparation Example 1

Preparation of Injections

10 μg of echstatin was dissolved in 1 ml of water and a water soluble excipient,sucrose, was added so as to be at 1.25–40 w/v %. It was sterilely filtered by means of a 0.22 μm filter (available from Milipore Inc.). It was added in portions to vessels, freeze-dried and sealed to form preparations.

The promoting action of bone formation by the present agent will be illustrated by way of the following test results.
Test Result 1

Calvaria was excised from rat fetus of 20 days old and osteoblast-like cells were prepared by enzymatic treatment. The osteoblast-like cells were incubated in MEMα(+) medium containing 100 μl/ml ascorbic acid, 2 mM β-glycerol phosphate and 10% bovine fetal serum to form bone tuberculum. For bone tuberculum formation by the primary cultured osteoblasts, kistrin and echstatin did promote calcification and the number of bone tuberculum at $10^{-7}$ and $10^{-8}$M. Promoted alkaline phosphatase activity was observed at $10^{-8}$M.

Cyclic synthetic peptides, the compounds of the formulae (IV), (VII), (VIII) and (V) did promote calcification and the number of bone tuberculum at $10^{-6}$ and $10^{-8}$M. The compound of the formula (III) did promote calcification at $10^{-8}$ and $10^{-10}$M, and did the number of bone tuberculum at $10^{-6}$M. The GRGDS did promote calcification at $10^{-6}$M, but completely prevented calcification at $10^{-4}$M.
Test Result 2

Bone tuberculum formation by osteoblasts of rat fetal calvaria.

1) Preparation of enzyme solution 100 mg of collagenase (0.2%) and 50 mg of hyaluronidase (0.1%) were weighed out and added to 50 ml of bovine fetal serum-free F12 medium and stirred with a stirrer. It was sterilely filtered with a 0.22 μm filter and then applied.

2) Preparation and cultivation of osteoblasts

Fetuses of 20 days old (about 14 fetuses) were taken out from pregnant rat and immersed in 70% ethanol. Calvaria was exposed by removing scalp using nose-bent forceps and nose-bent scissors. Calvaria was cut out without removing periosteum and immersed in a bovine fetal serum-free medium. Connective tissues traveling toward front and rear in the central area and surrounding soft tissues were cut off using a scalpel. All bone pieces thus prepared were placed into a 50 ml centrifugal tube. 10 ml of the enzyme solution was added and the tube was shaken in a thermostat at 37° C. for 5 minutes. The treated liquid with dispersed cells was recovered and centrifuged at 1200 rpm for 5 minutes followed by removing a supernatant. 15 ml of F12, 10% FCS medium was added and cells were untied well and then spread on a 10 cm petri dish, which was defined as Fraction 1. To the bone pieces after recovering the treated liquid of the Fraction 1 was added 10 ml of the enzyme solution and shaken in a thermostat at 37° C. for 10 minutes. After centrifugation, the resulting cells were defined as Fraction 2. Subsequently, the cells in those fractions up to Fraction 5 were obtained in the similar enzyme treatment as above and the cells of Fractions 3–5 were incubated in a carbon dioxide incubator for 2–3 days using F12 medium containing 10% bovine fetal serum. After incubation, the cells were recovered by treating with 0.25% trypsin (EDTAfree). After counting the number of cells, cells were innoculated to a 4-well incubation plate (Nunc) at 1900 cells/300 μl (1000 cells/cm²) and incubation was continued for a further 2–3 days. After incubation, all cultured liquid was removed, 300 μl of the medium containing the active compound or dexamethasone ($10^{-8}$M) instead was added and then incubation was continued for 14 days. For the incubation from this point, the MEMα(+) medium containing 100 μl/ml ascorbic acid, 2 mM β-glycerol phosphate and 10% bovine fetal serum optimum for calcification was used. The medium was exchanged every 2 days and the active compound was added at every exchange. Area of the calcified region and the number of bone tuberculum were used as an index for bone tuberculum formation. After incubation, the cells were fixed with 10% formalin/phosphate buffered physiological saline for 60 minutes and then washed three times with distilled water. Thereafter, calcium phosphate in bone tuberculum was stained by treating with a 1% alizarin red stain for 10 minutes and washed three times with distilled water.

The area of the stained bone tuberculum was measured using Nikonruzex 3U image analysis device, while the number of bone tuberculum was counted visually under microscope.

3) Alkaline phosphatase activity

The cells incubated in the same manner as in the above 2) were washed twice with 500 μl of phosphate-buffered physiological saline and 300 μl of the eluent (1% Triton X-100, 0.5 mM magnesium chloride, 10 mM Tris, pH 7.2) was added and the mixture was allowed to stand on ice for 3 minutes. It was then transferred into Eppendorf tube, homogenized by means of a homogenizer and allowed to stand in a thermostat at 37° C. overnight to elute alkaline phosphatase. Subsequently, residues of cells and extracellular stroma were removed by centrifuging at 12000 rpm for 10 minutes and 10 $\mu$l of a supernatant was taken into another tube. 190 $\mu$l of an alkaline phosphatase substrate solution (100 mM 2-amino-2-methyl-1-propanol, 2 mM magnesium chloride and 2 mM sodium p-nitrophenylphosphate) was added and allowed to react in a thermostat at 37° C. for 10 minutes. Reaction was discontinued by addition of 800 $\mu$l of a 1N sodium hydroxide solution and absorbance was measured at a wave length of 405 nm.

Alkaline phosphatase activity was calculated according to the following equation:

$$\text{Alkaline phosphatase activity } (\mu\text{mole/min/well}) = \frac{(\text{Absorbance of sample} - \text{absorbance of blank}) \times 0.05714}{10 \text{ (minutes)}} \times \frac{300}{10}$$

The results of the bone tuberculum formation effect observed in the primary cultured osteoblasts are shown in Table 1.

TABLE 1

| Treatment | Calcified area (mm²/well) | No. of bone tuberculum (per well) | Alkaline phosphatase activity ($\mu$M/min/well) |
|---|---|---|---|
| Non-treated | 2.37 ± 0.98 | 146.5 ± 10.9 | 0.044 ± 0.014 |
| Dexamethasone | 8.00 ± 0.20 | 307.3 ± 34.1 | 0.181 ± 0.018 |
| Kistrin | | | |
| $10^{-6}$M | 0.01 ± 0.02 | 147.8 ± 14.2 | 0.040 ± 0.003 |
| $10^{-7}$M | 3.95 ± 0.82 | 189.5 ± 16.3 | 0.051 ± 0.007 |
| $10^{-8}$M | 4.03 ± 0.67 | 161.8 ± 19.2 | 0.067 ± 0.005 |
| $10^{-9}$M | 3.14 ± 0.95 | 153.8 ± 12.3 | 0.051 ± 0.008 |
| Echstatin | | | |
| $10^{-6}$M | 0.00 ± 0.00 | 179.0 ± 17.9 | 0.042 ± 0.007 |
| $10^{-7}$M | 3.89 ± 0.54 | 195.3 ± 16.0 | 0.046 ± 0.006 |
| $10^{-8}$M | 4.82 ± 0.64 | 180.5 ± 13.7 | 0.067 ± 0.001 |
| $10^{-9}$M | 3.13 ± 0.51 | 153.8 ± 12.3 | 0.053 ± 0.010 | mean ± standard deviation (n = 4)

In a positive control, the dexamethasone-medicated group, noticeable promoting effects were observed in all of the area of the calcined region, the number of bone tuberculum and the alkaline phosphatase activity, as compared with the non-treated group. Kistrin and echstatin did promote calcification and the number of bone tuberculum at $10^{-7}$ and $10^{-8}$M, whereas they prevented completely calcification at $10^{-6}$M, but were not observed to affect the number of bone tuberculum. Also, they were observed to promote alkaline phosphatase activity at $10^{-8}$M.

The results of the effect by the compounds of the formulae (III), (IV), GH 4, GH 5 and (V) are shown in Table 2.

TABLE 2

| Treatment | Calcified area (mm²/well) | No. of bone tuberculum (per well) |
|---|---|---|
| Non-treated | 2.37 ± 0.98 | 146.5 ± 10.9 |
| Dexamethasone | 8.00 ± 0.20 | 307.3 ± 34.1 |

TABLE 2-continued

| Treatment | Calcified area (mm²/well) | No. of bone tuberculum (per well) |
|---|---|---|
| Formula (III) | | |
| $10^{-4}$M | 0.00 ± 0.00 | 164.5 ± 12.0 |
| $10^{-6}$M | 1.82 ± 0.49 | 177.5 ± 11.4 |
| $10^{-8}$M | 3.67 ± 0.54 | 162.8 ± 31.0 |
| $10^{-10}$M | 4.39 ± 0.65 | 158.0 ± 28.7 |
| Formula (IV) | | |
| $10^{-4}$M | 1.82 ± 0.46 | 182.8 ± 22.8 |
| $10^{-6}$M | 4.99 ± 0.84 | 194.3 ± 8.1 |
| $10^{-8}$M | 5.58 ± 0.95 | 194.8 ± 19.3 |
| $10^{-10}$M | 3.13 ± 0.67 | 157.0 ± 17.6 |
| GH4 | | |
| $10^{-4}$M | 0.00 ± 0.00 | 152.3 ± 8.5 |
| $10^{-6}$M | 4.24 ± 0.55 | 196.0 ± 16.3 |
| $10^{-8}$M | 5.64 ± 0.81 | 184.8 ± 23.7 |
| $10^{-10}$M | 3.78 ± 0.47 | 166.0 ± 17.0 |
| GH5 | | |
| $10^{-4}$M | 0.00 ± 0.00 | 207.5 ± 18.9 |
| $10^{-6}$M | 4.00 ± 0.81 | 211.8 ± 14.5 |
| $10^{-8}$M | 5.88 ± 0.78 | 204.8 ± 22.9 |
| $10^{-10}$M | 4.51 ± 0.57 | 155.0 ± 13.5 |
| Formula (V) | | |
| $10^{-4}$M | 0.00 ± 0.00 | 148.8 ± 15.2 |
| $10^{-6}$M | 3.37 ± 0.48 | 182.8 ± 22.8 |
| $10^{-8}$M | 3.47 ± 0.75 | 174.8 ± 23.7 |
| $10^{-10}$M | 2.41 ± 0.99 | 158.5 ± 23.6 |
| GRGDS | | |
| $10^{-4}$M | 0.00 ± 0.00 | 168.3 ± 17.1 |
| $10^{-6}$M | 3.74 ± 0.95 | 166.5 ± 10.6 | mean ± standard deviation (n = 4)

The compounds of the formula (IV), GH 4, GH 5 and the formula (V) did promote calcification and the number of bone tuberculum at $10^{-6}$ and $10^{-8}$M. The compounds of the formula (III), GH 4, GH 5 and the formula (V) did completely prevent calcification at $10^{-4}$M, but were not observed to affect the number of bone tuberculum. The compound of the formula (III) did promote calcification at $10^{-8}$ and $10^{-10}$M and did promote the number of bone tuberculum at $10^{-6}$M. The GRGDS (SEQ ID NO: 1) did promote calcification at $10^{-6}$M, but did completely prevent calcification at $10^{-4}$M. The number of bone tuberculum was observed to show a tendency to be increased at these concentrations.

Kistrin and Compound No. 43 were tested using the bone tuberculum formation test as described above. The results are shown in Table 3.

TABLE 3

| Treatment | Calcified area (mm²/well) | Alkaline phosphatase activity ($\mu$M/min/well) |
|---|---|---|
| Non-treated | 4.46 ± 0.83 | 0.084 ± 0.008 |
| Dexamethasone | | |
| $10^{-8}$M | 13.82 ± 1.20 | 0.143 ± 0.015 |
| Kistrin | | |
| $10^{-5}$M | 4.54 ± 0.88 | 0.085 ± 0.009 |
| $10^{-6}$M | 7.93 ± 1.37 | 0.119 ± 0.008 |
| $10^{-7}$M | 11.25 ± 1.04 | 0.133 ± 0.006 |
| $10^{-8}$M | 9.87 ± 1.04 | 0.126 ± 0.006 |

TABLE 3-continued

| Treatment | Calcified area ($mm^2$/well) | Alkaline phosphatase activity ($\mu M$/min/well) |
|---|---|---|
| Compound No. 43 | | |
| $10^{-5}$M | 4.83 ± 0.87 | 0.088 ± 0.008 |
| $10^{-6}$M | 7.31 ± 0.69 | 0.108 ± 0.005 |
| $10^{-7}$M | 8.45 ± 0.66 | 0.099 ± 0.004 |
| $10^{-8}$M | 6.29 ± 0.43 | 0.100 ± 0.003 | mean ± standard deviation (n = 4)

Compound No. 63 was tested using the bone tuberculum formation test as described above. The results are shown in Table 4.

TABLE 4

| Treatment | Calcified area ($mm^2$/well) |
|---|---|
| Non-treated | 2.56 ± 0.11 |
| Dexamethasone | |
| $10^{-8}$M | 12.17 ± 1.05 |
| Compound No. 63 | |
| $10^{-5}$M | 1.62 ± 0.55 |
| $10^{-6}$M | 4.26 ± 2.14 |
| $10^{-7}$M | 5.14 ± 1.29 |
| $10^{-8}$M | 3.84 ± 1.06 | mean ± standard deviation (n = 4)

Effect of the Invention

An agent for promoting bone formation, which comprises as an active ingredient a peptide or polypeptide having the amino acid sequence composed of ArgGlyAsp in the molecule such as kistrin, echstatin, a peptide represented by Gly-Arg-Gly-Asp-Ser (SEQ ID NO: 1), a compound of the above formula (I) or (II), or a compound of the formula (IX), (X), (XI) or (XII), can be administered to human body or implanted into the area close to the fractured bone to accomplish effective prophylaxis and therapy of bone fracture.

What is claimed is:

1. A method of promoting bone formation in humans comprising administering to humans an amount of at least one compound selected from the group consisting of kistrin, echstatin and Gly-Arg-Gly-Asp-Ser or a compound having a formula selected from the group consisting of

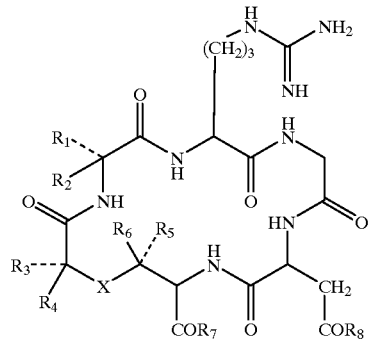

I

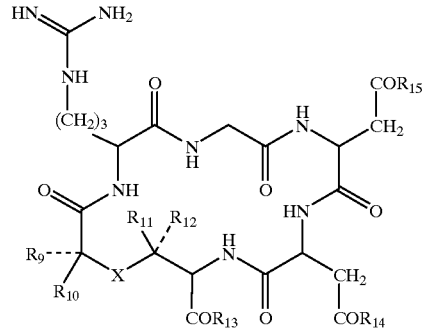

II

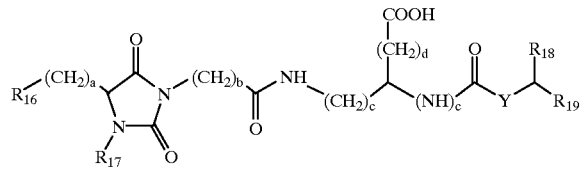

IX

SEQUENCE LISTING

<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1

Gly Arg Gly Asp Ser
1               5

X

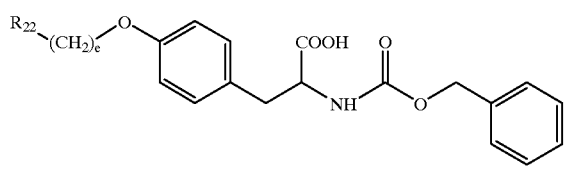

XI

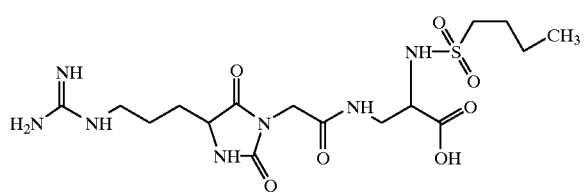

XII

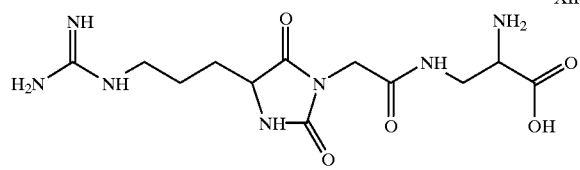

and pharmaceutically acceptable salts thereof sufficient to promote bone formation wherein $R_1$, $R_2$, $R_3$, $R_4$, $R_5$ and $R_6$ are individually selected from the group consisting essentially of a) hydrogen, b) alkyl of 1 to 8 carbon atoms unsubstituted or substituted with a member of the group consisting of —OH, —COOH, cycloalkyl of 3 to 10 carbon atoms, hydroxy cycloalkyl of 3 to 10 carbon atoms, aryl of 6 to 12 carbon atoms and hydroxy aryl of 6 to 12 carbon atoms, and c) cycloalkyl of 3 to 10 carbon atoms, hydroxy cycloalkyl of 3 to 10 carbon atoms, aryl of 6 to 12 carbon atoms and hydroxy aryl of 6 to 12 carbons, $R_7$, $R_8$, $R_{13}$, $R_{14}$ and $R_{15}$ are individually selected from the group consisting of —OH, alkoxy of 1 to 8 carbon atoms, alkenyloxy of 2 to 12 carbon atoms, cycloalkoxy of 3 to 10 carbon atoms and aryloxy of 6 to 12 carbon atoms, X is —S— or —SO—, $R_9$, $R_{10}$, $R_{11}$, and $R_{12}$ are individually selected from the group consisting essentially of hydrogen, alkyl of 1 to 8 carbon atoms, cycloalkyl of 3 to 10 carbon atoms, hydroxyaryl of 6 to 12 carbon atoms and aryl of 6 to 12 carbon atoms, $R_{16}$ is selected from the group consisting of —N—$(R_{20})_2$,

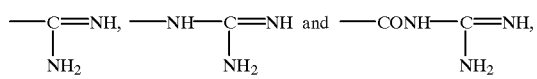

$R_{17}$ is hydrogen or alkyl of 1 to 4 carbon atoms or phenyl alkyl of 1 to 4 alkyl carbon atoms, $R_{18}$ is selected from the group consisting of hydrogen, alkyl of 1 to 4 carbon atoms, phenyl and phenyl substituted with —OCH$_3$ or —COR$_{21}$, $R_{19}$ is alkyl of 1 to 15 carbon atoms or alkyl of 1 to 5 carbon atoms substituted with a member of the group consisting of —OH, —NH$_2$, —CONH$_2$, cyclohexyl, phenyl, naphthyl, indolyl, adamantyl, methyl substituted with —COOH, —NHCOOCH$_2$-phenyl, cyclohexyl, methoxy cyclohexyl, aryl of 6 to 10 carbon atoms and methoxy aryl of 6 to 10 carbon atoms or $R_{18}$ and $R_{19}$ together with the carbon atoms to which they are attached form a member of the group consisting of adamantyl, naphthyl and fluorenyl, $R_{20}$ is hydrogen or alkyl of 1 to 4 carbon atoms or alkylphenyl of 1 to 4 alkyl carbon atoms, $R_{21}$ is selected from the group consisting of —OH, —NH$_2$, —NH—CH$_2$—CH$_2$-phenyl, alkoxy of 1 to 3 carbon atoms, benzyloxy, Pro and Aoc, Y is selected from the group consisting of —NH—, —O— and a bond, a is an integer from 1 to 3, b is 1 or 2, c is 0 or 1, d is 0 or 1, $R_{22}$ is selected from the group consisting of —N$(R_{23})_2$,

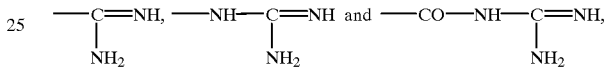

$R_{23}$ is hydrogen or alkyl of 1 to 4 carbon atoms or phenyl alkyl of 1 to 4 alkyl carbon atoms and e is an integer from 2 to 6.

2. The method of claim 1 wherein the compound is kistrin.

3. The method of claim 1 wherein the compound is Gly-Arg-Gly-Asp-Ser.

4. The method of claim 1 wherein the compound is echstatin.

5. A method of promoting bone formation in humans comprising administering to humans an amount of a compound of a formula selected from the group consisting of

III

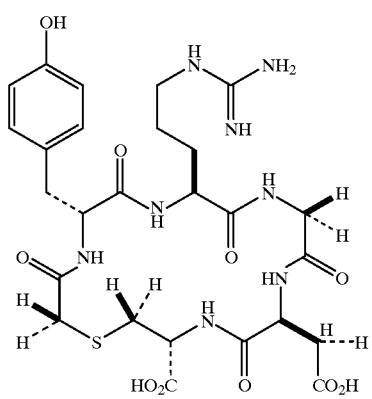

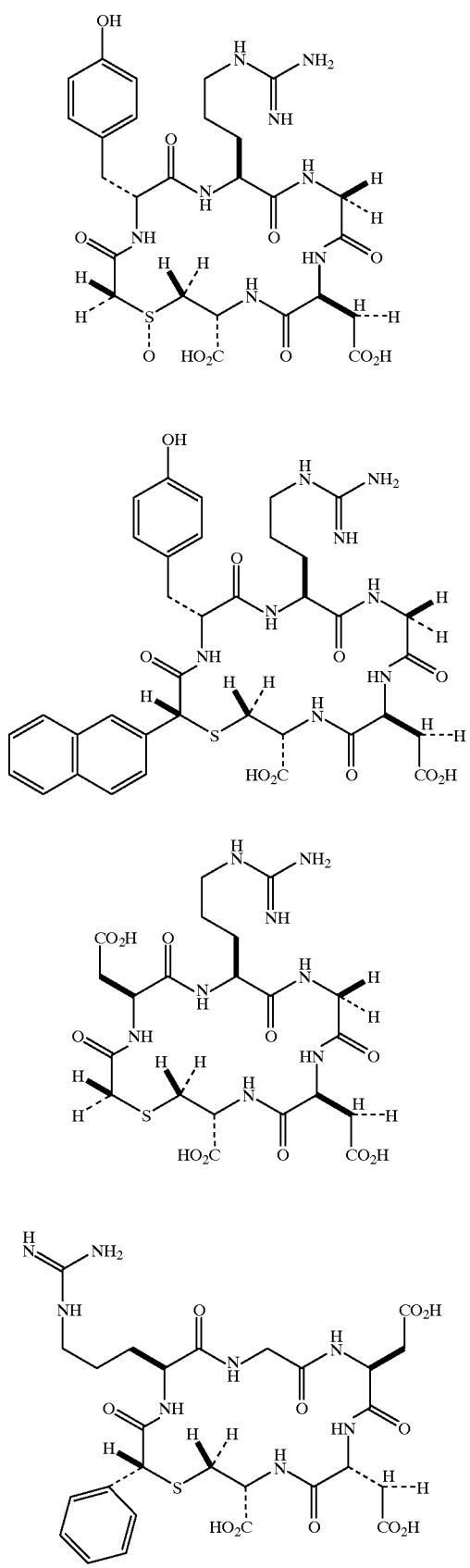

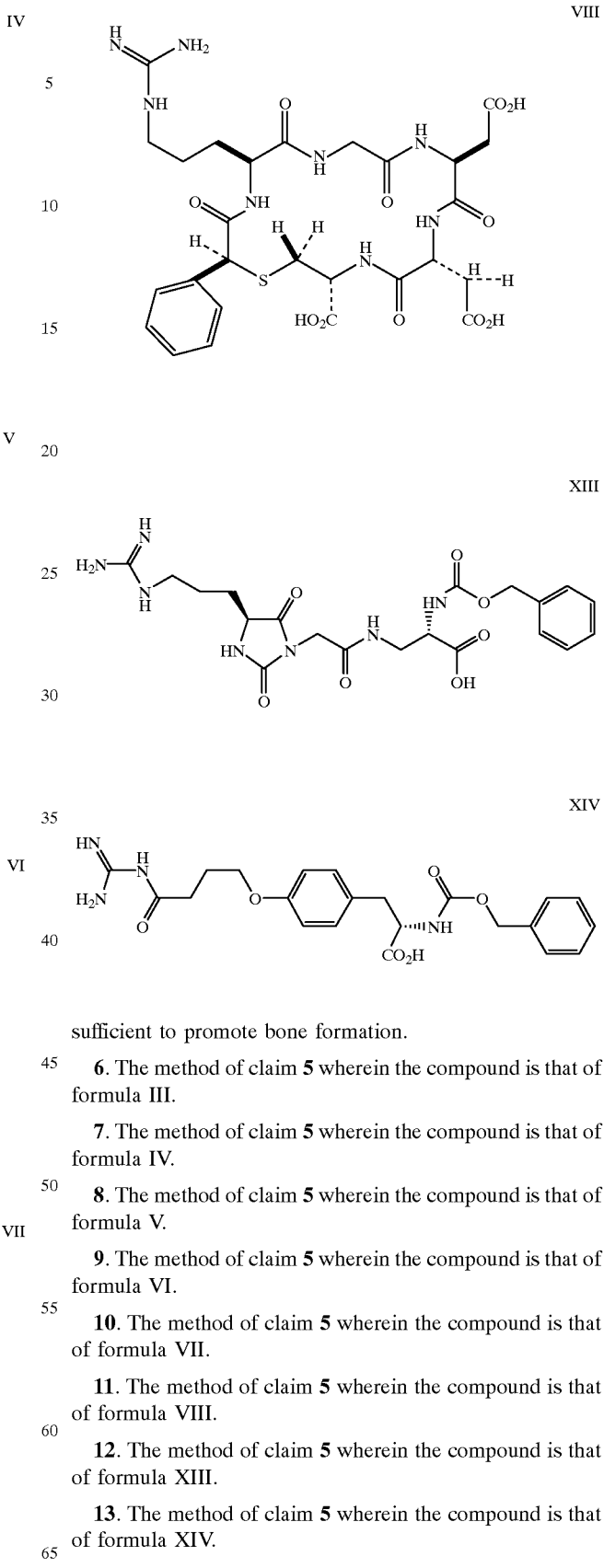

sufficient to promote bone formation.

6. The method of claim 5 wherein the compound is that of formula III.

7. The method of claim 5 wherein the compound is that of formula IV.

8. The method of claim 5 wherein the compound is that of formula V.

9. The method of claim 5 wherein the compound is that of formula VI.

10. The method of claim 5 wherein the compound is that of formula VII.

11. The method of claim 5 wherein the compound is that of formula VIII.

12. The method of claim 5 wherein the compound is that of formula XIII.

13. The method of claim 5 wherein the compound is that of formula XIV.

* * * * *